(12) United States Patent
Kino et al.

(10) Patent No.: US 6,706,517 B2
(45) Date of Patent: Mar. 16, 2004

(54) METHOD FOR PRODUCING L-AMINO ACIDS BY FERMENTATION

(75) Inventors: Kuniki Kino, Chiba (JP); Tetsuya Abe, Hofu (JP)

(73) Assignee: Kyowa Hakko Kogyo Co., Ltd., Tokyo (JP)

(*) Notice: Subject to any disclaimer, the term of this patent is extended or adjusted under 35 U.S.C. 154(b) by 0 days.

(21) Appl. No.: 10/024,190

(22) Filed: Dec. 21, 2001

(65) Prior Publication Data

US 2002/0102665 A1 Aug. 1, 2002

Related U.S. Application Data

(62) Division of application No. 09/663,795, filed on Sep. 18, 2000, now Pat. No. 6,344,347.

(30) Foreign Application Priority Data

Sep. 20, 1999 (JP) .......................................... 11-265107

(51) Int. Cl.[7] .......................... C12N 1/20; C12P 13/04; C12P 13/24
(52) U.S. Cl. .................. 435/252.8; 435/106; 435/107; 435/252.33; 435/252.5; 435/253.1; 435/830; 435/832; 435/839; 435/843; 435/849; 435/880; 435/881
(58) Field of Search .................. 435/252.1, 252.33, 435/252.8, 849

(56) References Cited

U.S. PATENT DOCUMENTS

| | | | |
|---|---|---|---|
| 4,388,405 A | 6/1983 | Sano et al. | 435/107 |
| 4,442,208 A | 4/1984 | Tsuchida et al. | 435/116 |
| 4,463,094 A | 7/1984 | Chibata et al. | 435/115 |
| 4,504,581 A | 3/1985 | Kurahashi et al. | 435/107 |
| 4,601,983 A | 7/1986 | Nakamori et al. | 435/115 |
| 4,775,623 A | 10/1988 | Katsumata et al. | 435/114 |
| 4,874,698 A | 10/1989 | Ozaki et al. | 435/108 |
| 4,908,312 A | 3/1990 | Ozaki et al. | 435/108 |
| 4,927,758 A | 5/1990 | Mizukami et al. | 435/107 |
| 5,017,483 A | 5/1991 | Furukawa et al. | 435/115 |
| 5,264,353 A | 11/1993 | Yamada et al. | 435/115 |
| 5,275,940 A | 1/1994 | Kino et al. | 435/108 |

FOREIGN PATENT DOCUMENTS

| | | |
|---|---|---|
| EP | 473094 | 3/1992 |
| JP | 50031093 | of 1975 |
| JP | 77048195 | of 1978 |
| JP | 81010037 | of 1981 |
| JP | 60210994 | of 1985 |
| JP | 61195695 | 8/1986 |
| JP | 61271981 | 12/1986 |
| JP | 2000458 | 1/1990 |
| JP | 2042988 | 2/1990 |
| JP | 4330275 | of 1992 |
| JP | 93026467 | 4/1993 |

OTHER PUBLICATIONS

Ivanisevic et al "Journal of Bacteriology" Apr. 1995 pp. 1766–1771.*
Filutowicz "Molec. gen. Genet" 1980, Vol 177, pp. 3–1–309.*
Computer CAPLUS Abstracct 1995:467923 Ivanisevic et al"J. Bacteriol" (1995) 177(7) 1766–71.*
Computer Biosis Abstract 1980:209873 Filutowicz "Mol Gen Genet" (1980) 177(2) 301–310.*
Computer EMBASE Abstract 78317726 Drlica et al "Jour Molecular Biology" (1978) 120/2 (145–154).*
Computer EMBASE Abstract 90121912 Hallett et al "Mol Microbiol" (1990) 4/3 (345–353).*
Title pages and p. 206 pf Coombs, ed., Macmillan Dictionary of Biotechnology, The Macmillan Press Ltd., 1986.
Stein, D.C., et al, "Characterization of *gyrB* Mutation Responsible for Low–Level Nalidixic Acid Resistance in *Neisseria Gonorrhoeae*" Antimicrobial Agents and Chemotherapy, American Society for Microbiology, Washington, D.C., vol. 35, No. 4, Apr. 1991, pp. 622–626, XP001005630, ISSN 0066–4804.
Munoz R. et al., "Ser–127–To0Leu Substitution in the DNA Gyrase B Subunit of *Strepococcus pneumoniae* is implicated in Novobiocin Resistance" Journal of Bacteriology, Washington, D.C., vol. 177, No. 14, Jul. 1995 pp. 4166–4170, XP000829551 ISSN: 0021–9193.
Lewis, J. A. and Ames, B. N.: "Histidine Regulation in *Salmonella typhimurium* XI.", J. Mol. Biol., vol. 66, 1972, pp. 131–142, XP001119966.
Rudd, K. E. and Menzel, R.: "his operons of *Escherichia coli* and *Salmonella typhimurium* are regulated by DNA supercoiling" Proc. Natl. Acad. Sci. USA vol. 84 1987, pp. 517–521, XP001120171.
Rudd KE, et al, "his operons of *Escherichia coli* and *Salmonella typhimurium* are regulated by DNA supercoiling", Proc. Natl. Acad. Sci. USA, vol. 84, pp 517–521(1987).
Lewis, JA et al, "Histidine Regulation in *Salmonella typhimurium*" J. Mol. Biol, vol. 66, pp 131–142 (1972).
Davidson, et al, "Regulation of Isoleucine and Valine Biosynthesis in *Salmonella typhimurium*: The effect of *hisU* on Repression Control". J. Mol. Biol., vol. 127, pp 229–235 (1979).
Davis, L et al, "Altered Regulationof Isoleucine–Valine Biosynthesis in a *hisW* Mutant of *Salmonella typhimurium*", Journal of Bacteriology, vol. 151, pp 860–866(1982).

* cited by examiner

*Primary Examiner*—Herbert J. Lilling
(74) *Attorney, Agent, or Firm*—Antonelli, Terry, Stout & Kraus, LLP

(57) ABSTRACT

The present invention provides an industrially efficient method for producing an L-amino acid useful as medicament, chemical agent, food material and feed additive, and the method comprising culturing in a medium a microorganism having an ability to produce the L-amino acid and having resistance to a DNA gyrase inhibitor or a microorganism having an ability to produce the L-amino acid and having both resistance to a DNA gyrase inhibitor and resistance to an aminoquinoline derivative, producing and accumulating the L-amino acid therein and recovering the L-amino acid therefrom.

7 Claims, No Drawings

METHOD FOR PRODUCING L-AMINO ACIDS BY FERMENTATION

CROSS REFERENCE TO RELATED APPLICATIONS

This application is a Divisional Application of application Ser. No. 09/663,795 filed Sep. 18, 2000 now U.S. Pat. No. 6,344,347.

BACKGROUND OF THE INVENTION

The present invention relates to a method for producing an L-amino acid by fermentation at high industrial efficiency.

As a direct fermentation method for producing and accumulating an L-amino acids directly from saccharide, there have been known methods in which mutant strains derived from wild-type strains of microorganism belonging to the genus Corynebacterium, Brevibacterium, Escherichia, Serratia or Arthrobacter are employed. For example, the following are known as L-amino acid-producing mutants: auxotrophic mutants which require amino acids, etc. (Japanese Published Examined Patent Application No. 10037/1981), mutants which have resistance to amino acid analogs and vitamins (Japanese Published Unexamined Patent Application Nos. 134993/1981 and 44193/1987), mutants which have both auxotrophic mutation and resistance mutation to amino acid analog(Japanese Published Unexamined Patent Application Nos. 31093/1975 and 134993/1981), mutants which have lowered degradability (Japanese Published Unexamined Patent Application No. 273487/1988, and Japanese Published Examined Patent Application No. 48195/1977), and mutants whose aminoacyl t-RNA-synthesizing enzymes have a decreased substrate affinity (Japanese Published Unexamined Patent Application No. 330275/1992).

It has also been known that the production of an amino acid can be improved by using transformants obtained by transformation with recombinant DNAs carrying genes involved in the biosynthesis of amino acids (Japanese Published Unexamined Patent Application Nos. 893/1983, 12995/1985, 210994/1985, 30693/1985, 195695/1986, 271981/1986, 458/1990 and 42988/1990; Japanese Published Examined Patent Application s. 42676/1989, 11960/1993 and 26467/1993).

For producing L-tryptophan, there has been a report that the productivity of the amino acid was improved by giving resistance to aminoquinoline derivatives or to phenothiazine derivatives (Japanese Published Unexamined Patent Application No. 112795/1992).

There have been a report that the expression of an operon involved in histidine synthesis is increased in a DNA gyrase-deficient strain [*Proc. Natl. Acad. Sci. USA*, 84, 517 (1987)] and a report that the levels of some amino acid t-RNA species including His-tRNA are decreased in a DNA gyrase mutant strain [*J. Mol. Biol.*, 66, 131 (1972)], however, no report has been made yet about the relation between resistance to DNA gyrase inhibitors and amino acid productivity.

SUMMARY OF THE INVENTION

An object of the present invention is to provide an industrially efficient method for producing an L-amino acid useful as medicament, chemical agent, food material and feed additive.

The present invention relates to the following aspects (1) to (14).

(1) A method for producing an L-amino acid, which comprises:
   (a) culturing in a medium a microorganism having an ability to produce an L-amino acid and having resistance to a DNA gyrase inhibitor;
   (b) producing and accumulating the L-amino acid in the culture; and
   (c) recovering the L-amino acid from the culture.

(2) The method for producing an L-amino acid as described above in (1), wherein the DNA gyrase inhibitor is selected from the group consisting of nalidixic acid, oxolinic acid, coumermycin, novobiocin and the alkali metal salts of these substances.

(3) The method for producing an L-amino acid as described above in (1), wherein the microorganism has resistance to an aminoquinoline derivative.

(4) The method for producing an L-amino acid as described above in (3), wherein the aminoquinoline derivative is selected from the group consisting of chloroquine, amodiaquine, pentaquine, primaquine and the alkali metal salts of these substances.

(5) The method for producing an L-amino acid as described above in any one of (1) to (4), wherein the L-amino acid is L-histidine.

(6) The method for producing an L-amino acid as described above in (1) or (3), wherein the microorganism is selected from the group consisting of genera Serratia, Corynebacterium, Arthrobacter, Microbacterium, Bacillus and Escherichia.

(7) The method for producing an L-amino acid as described above in (6), wherein the microorganism is selected from the group consisting of *Escherichia coli* H-9342 (FERM BP-6675) and *Escherichia coli* H-9343 (FERM BP-6676).

(8) A microorganism having an ability to produce an L-amino acid and having resistance to a DNA gyrase inhibitor.

(9) The microorganism described above in (8), wherein the DNA gyrase inhibitor is selected from the group consisting of nalidixic acid, oxolinic acid, coumermycin, novobiocin, and the alkali metal salts of these substances.

(10) The microorganism described above in (8) or (9), wherein the microorganism has resistance to an aminoquinoline derivative.

(11) The microorganism described above in (10), wherein the aminoquinoline derivative is selected from the group consisting of chloroquine, amodiaquine, pentaquine, primaquine, and the alkali metal salts of these substances.

(12) The microorganism described above in (8), wherein the L-amino acid is L-histidine.

(13) The microorganism described above in any one of (8) to (12), wherein the microorganism is selected from the group consisting of genera Serratia, Corynebacterium, Arthrobacter, Microbacterium, Bacillus, and Escherichia.

(14) A microorganism selected from either *Escherichia coli* H-9342 (FERM BP-6675) or *Escherichia coli* H-9343 (FERM BP-6676).

DETAILED DESCRIPTION OF THE INVENTION

As the microorganism of the present invention, any microorganism can be used, so long as it has an ability to produce an L-amino acid and has resistance to the DNA gyrase inhibitor. Additionally, it is preferable that the microorganism has further resistance to an aminoquinoline derivative. Examples of the microorganism include microorganisms belonging to the genus Serratia, Corynebacterium, Arthrobacter, Microbacterium, Bacillus, or Escherichia, such as *Serratia ficaria, Serratia fonticola, Serratia liquiefaciens, Serratia marcescens, Corynebacterium glutamicum, Corynebacterium mycetoides, Corynebacterium variabilis, Corynebacterium ammoniagenes, Arthrobacter crystallopoietes, Arthrobacter duodecadis, Arthrobacter ramosus, Arthrobacter sulfureus, Arthrobacter aurescens, Arthrobacter citreus, Arthrobacter globiformis, Microbacterium ammoniaphilum, Bacillus subtilis, Bacillus amyloliquefacines* and *Escherichia coli.*

As the DNA gyrase inhibitor for use in the present invention, any substance can be used, so long as it inhibits DNA gyrase, one of the type II topoisomerases which are present in bacteria. For example, nalidixic acid, oxolinic acid, coumermycin and novobiocin can be used as the DNA gyrase inhibitor. Additionally, the alkali metal salts of these substances can be used as the DNA gyrase inhibitor. Herein, any alkali metal such as sodium and potassium can be used as the alkali metals.

As the aminoquinoline derivative for use in the present invention, any substance can be used, so long as it has the aminoquinoline skeleton. For example, 4-aminoquinoline derivatives such as chloroquine and amodiaquine and 8-aminoquinoline derivatives such as pentaquine and primaquine can be used as the aminoquinoline derivative. Additionally, the alkali metal salts of these substances can be used as the aminoquinoline derivative. All of these substances are known as antimalarial drugs. Herein, any alkali metal such as sodium and potassium can be used as the alkali metals.

The microorganism of the present invention can be obtained by subjecting a microorganism having an ability to produce an L-amino acid to a conventional mutation treatment including ultraviolet irradiation and the treatment with mutagen such as N-methyl-N'-nitro-N-nitrosoguanidine (NTG), culturing the resulting mutant strains under general conditions on an agar plate medium containing a DNA gyrase inhibitor at a concentration at which the parent strain cannot grow or grow poorly, and selecting colonies which grow more rapidly than that of the parent strain or colonies which are larger than the parent strain among the resulting colonies.

Further, the microorganism having both resistance to a DNA gyrase inhibitor and resistance to an aminoquinoline derivative can be obtained by subjecting the DNA gyrase inhibitor-resistant strain to a mutation treatment, culturing the resulting mutant strains on an agar plate medium containing an aminoquinoline derivative at a concentration at which the parent strain cannot grow or grows poorly, and selecting colonies which are larger than the parent strain among the resulting colonies.

As the microorganism having an ability to produce the amino acid, a microorganism inherently having an ability to produce the amino acid can be used; alternatively, a microorganism which is newly obtained by subjecting a wild-type of a microorganism to produce the amino acid by known methods can also be used.

The known methods include cell fusion method, transduction method, and other gene recombinant techniques [for all, see *Molecular Cloning, A Laboratory Manual, Second Edition*, Cold Spring Harbor Laboratory Press (1989) (abbreviated as *Molecular Cloning*, 2nd ed. hereinbelow)], in addition to the above mutation treatment.

The microorganism of the present invention can also be obtained, by preparing a microorganism having resistance to a DNA gyrase inhibitor or a microorganism having both resistance to a DNA gyrase inhibitor and resistance to an aminoquinoline derivative by conventional mutation treatment and then by subjecting the prepared mutant microorganism to the above-described method to confer on the microorganism an ability to produce an L-amino acid.

Specific examples of the microorganisms of the present invention include *Escherichia coli* H-9342 (FERM BP-6675) and *Escherichia coli* H-9343 (FERM BP-6676).

The production of the L-amino acid by using the microorganism of the present invention can be carried out by an conventional method for culturing bacteria.

As the medium used for the production of L-amino acid, any of medium may be used, so long as it appropriately contains a carbon source, a nitrogen source, an inorganic substance and trace amounts of nutrients which the strain requires.

As the carbon source, carbohydrates such as glucose, fructose, lactose, molasses, cellulose hydrolysates, crude saccharide hydrolysates and starch hydrolysates; organic acids such as pyruvic acid, acetic acid, fumaric acid, malic acid and lactic acid; and alcohol such as glycerin and ethanol can be used.

As the nitrogen source, ammonia; various inorganic salts such as ammonium chloride, ammonium sulfate, ammonium acetate and ammonium phosphate; ammonium salts of organic acids; amines; peptone, meat extract, corn steep liquor, casein hydrolysates, soybean cake hydrolysates, various fermented cells and digested matters thereof can be used.

As the inorganic substance, potassium dihydrogen phosphate, dipotassium hydrogen phosphate, magnesium phosphate, magnesium sulfate, magnesium chloride, sodium chloride, ferrous sulfate, manganese sulfate, copper sulfate, calcium chloride and calcium carbonate can be used.

The microorganism is cultured under aerobic conditions such as shaking culture and aerated agitation culture, at a temperature within a range of 20 to 40° C., preferably within a range of 28 to 37° C. The pH of the medium is within a range of 5 to 9, preferably around neutrality. The pH of the medium is adjusted by using calcium carbonate, inorganic or organic acids, alkali solutions, ammonia and pH buffers. Generally, the L-amino acid is produced and accumulated in the medium by culturing for 1 to 7 days.

After completion of the culturing, the precipitates such as cells are removed from the culture, and the L-amino acid can be recovered from the culture by means of ion exchange treatment method, concentration, etc., in combination.

In accordance with the present invention, any L-amino acid can be produced with no specific limitation, but includes for example L-histidine.

The present invention is further illustrated by the following Examples, which are not to be construed to limit the scope of the present invention.

EXAMPLE 1

Preparation of an L-histidine-producing mutant strain having resistance to a DNA gyrase inhibitor or an L-histidine-producing mutant strain having both resistance to a DNA gyrase inhibitor and resistance to an aminoquinoline derivative The L-histidine-producing mutant strain H-9340 having resistance to 1,2,4-triazole alanine, which was derived from methionine-requiring *Escherichia coli* ATCC 21318 was subjected to a mutation treatment with N-methyl-N'-nitro-N-nitrosoguanidine (NTG) (0.2 mg/ml, 30° C., 30 minutes) according to a conventional method and spread on a 1 g/liter noboviocin monosodium salt-containing agar plate medium [0.2% glucose, 0.3% potassium dihydrogen phosphate, 0.6% disodium hydrogen phosphate, 0.01% magnesium sulfate, 0.05% sodium chloride, 0.1% ammonium chloride, 50 mg/liter required nutrient (DL-methionine) and 1.5% agar, pH 7.2].

The mutant strain was cultured on the agar plate medium at 30° C. for 2 to 6 days, and the growing large colonies were picked up and separated to obtain the strain H-9342.

Furthermore, the obtained colony was subjected to a mutation treatment with NTG (0.2 mg/ml, 30° C., 30 minutes), followed by spreading on an agar plate culture medium containing 150 mg/liter primaquine disodium salt. Culturing was carried out thereon at 30° C. for 2 to 6 days, and growing large colonies were picked up and separated to obtain the strain H-9343. The strains H-9340, H-9342 and H-9343 were deposited on March 9, 1999 with the National Institute of Bioscience and Human-Technology, Agency of Industrial Science and Technology (1-3, Higashi 1-chome, Tsukuba-shi, Ibaraki-ken, Japan) under the Budapest Treaty with accession Nos. FERM BP-6673, FERM BP-6675 and FERM BP-6676, respectively.

EXAMPLE 2

Comparative test of growth on agar plate culture medium containing primaquine or novobiocin The growth of the mutant strains H-9342 and H-9343 obtained in Example 1 was compared with the growth of the parent strain H-9340 on an agar plate medium containing primaquine or novobiocin.

Each of the mutant strains, which had been cultured in a natural medium for 24 hours and suspended in physiological saline, was spread at a cell density of 1 to 10 cells/cm$^2$ on the agar plate medium containing primaquine disodium salt or novobiocin monosodium salt at the same concentration as that at the time of acquisition of each mutant strain, and cultured at 33° C. for 4 days.

Growth or non-growth of each strains on the above media is shown in Table 1.

The parent strain H-9340 did not grow on any agar plate culture medium containing either one of the chemical agents. Additionally, H-9342 did not grow on the primaquine-containing culture medium.

TABLE 1

| Bacterial strain | Additives for agar culture medium | | |
|---|---|---|---|
| | No addition | Primaquine disodium salt | Novobiocin monosodium salt |
| H-9340 | + | − | − |
| H-9342 | + | − | + |
| H-9343 | + | + | + |

EXAMPLE 3

Production of L-histidine

The production of L-histidine using the mutant strains H-9342 and H-9343 obtained in Example 1 and the parent strain H-9340 was carried out in the following manner.

Each of the strains H-9340, H-9342 and H-9343 was inoculated in 6 ml of a seed medium (2% glucose, 0.5% molasses, 1% corn steep liquor, 1.2% ammonium sulfate, 0.3% potassium dihydrogen phosphate, 0.015% magnesium sulfate, 600 mg/liter DL-methionine, 100 mg/liter adenine, 3% calcium carbonate, pH 6.2) in a large test tube, and cultured with shaking at 30° C. for 12 hours.

Each of the resulting seed cultures (0.1 ml) was inoculated in 5 ml of a production medium (6% glucose, 1% corn steep liquor, 2.4% ammonium sulfate, 0.4% potassium dihydrogen phosphate, 0.015% magnesium sulfate, 10 mg/liter thiamine chloride salt, 10 mg/liter calcium pantothenate, 3% calcium carbonate, pH 6.5) in a large test tube and was then cultured with shaking at 30° C. for 48 hours.

After culturing, the amount of L-histidine accumulated in the culture was assayed by high-performance liquid chromatography.

The results are shown in Table 2.

Compared with the L-histidine productivity of the parent strain H-9340, the L-histidine productivity of the mutant strain H-9342 was improved; and compared with the L-histidine productivity of the mutant strain H-9342, the L-histidine productivity of the mutant strain H-9343 was improved.

TABLE 2

| Bacterial strains | L-histidine (g/l) |
|---|---|
| H-9340 | 13.0 |
| H-9342 | 15.7 |
| H-9343 | 16.5 |

Furthermore, 100 ml of the seed culture of H-9343 was inoculated in 600 ml of a fermentation culture medium (6% glucose, 1% corn steep liquor, 0.5% ammonium sulfate, 0.4% potassium dihydrogen phosphate, 0.05% magnesium sulfate, 100 mg/liter calcium chloride, pH 6.5) in a 2-liter small fermentor, and the culturing was conducted at 30° C., at the rate of 800 rpm at an aeration volume of 1 liter/min. The pH adjustment and nitrogen source supply during culturing were carried out by using aqueous ammonia, to maintain the pH at 6.5±0.2. Under appropriate supply of glucose, ammonium sulfate and potassium dihydrogen phosphate, the culturing was conducted for 70 hours.

Consequently, the amount of L-histidine accumulated in the culture was 46.5 g/liter. On the other hand, the amount of L-histidine accumulated during the culturing of H-9340 in the same manner was 27.7 g/liter.

In accordance with the present invention, a microorganism having an ability to produce an L-amino acid and having resistance to a DNA gyrase inhibitor or a microorganism having an ability to produce an L-amino acid and having both resistance to a DNA gyrase inhibitor and resistance to an aminoquinoline derivative can be obtained and cultured in a medium, whereby the productivity of the L-amino acid can be improved so that the L-amino acid can be industrially efficiently produced at low cost.

What is claimed is:

1. A microorganism belonging to the genus Escherichia, having an ability to produce 15.7 g/l or more L-histidine and having resistance to 1 g/l novobiocin.

2. A microorganism belonging to the genus Escherichia, having an ability to produce and L-amino acid, and having resistance to a DNA gyrase inhibitor and to an aminoquinoline derivative, wherein the microorganism is obtained by subjecting a microorganism having an ability to produce an L-amino acid to a mutation treatment.

3. The microorganism according to claim 2, wherein the DNA gyrase inhibitor is selected from the group consisting of nalidixic acid, oxolinic acid, coumermycin, novabiocin and the alkali metal salts of these substances.

4. A mircroorganism according to claim 2, wherein the L-amino acid is L-histidine.

5. A microorganism belonging to the genus Escherichia, having an ability to produce L-histidine, and having resistance to a DNA gyrase inhibitor and an aminoquinoline derivative.

6. A microorganism selected from either *Escherichia coli* H-9342 (FERM BP-6675) or *Escherichia coli* H-9343 (FERM BP-6676).

7. The microorganism according to claim 2, wherein the aminoquinoline derivative is selected from the group consisting of chloroquine, amodiaquine, pentaquine, primaquine, and the alkali metal salts of these substances.

* * * * *